United States Patent [19]

Covington et al.

[11] 4,190,420
[45] Feb. 26, 1980

[54] CONTAINER FOR DISPENSING ARTICLES TO AN AUTOMATED ANALYZER

[75] Inventors: Roger G. Covington; Stephen H. Miller, both of Rochester; Archie J. Tucker, Middlesex, all of N.Y.

[73] Assignee: Eastman Kodak Company, Rochester, N.Y.

[21] Appl. No.: 912,289

[22] Filed: Jun. 5, 1978

[51] Int. Cl.² ............................ G01N 1/28; B65D 83/10
[52] U.S. Cl. ............................................ 422/63; 422/57; 422/104; 221/226; 221/230; 221/279
[58] Field of Search ............. 23/259, 253 R; 221/279, 221/220, 226, 229, 230, 231, 238; 422/57, 63, 102, 104

[56] References Cited

U.S. PATENT DOCUMENTS

| | | | |
|---|---|---|---|
| 757,993 | 4/1904 | Coleman et al. | 221/198 X |
| 1,120,907 | 12/1914 | Coffman | 221/152 X |
| 1,801,165 | 4/1931 | Macke | 221/238 |
| 3,533,744 | 10/1970 | Unger | 23/253 R |
| 3,767,083 | 10/1973 | Webb | 221/279 |
| 3,905,772 | 9/1975 | Hartnett et al. | 23/259 |

*Primary Examiner*—R. E. Serwin
*Attorney, Agent, or Firm*—M. S. Sales

[57] ABSTRACT

A container is disclosed for receiving a stack of articles to be sequentially removed from a dispensing station of the container. A stack positioning element in the container is movable forwardly in the container into engagement with an article stack to urge the forwardmost article forwardly toward the dispensing station. As articles are removed the stack positioning element normally moves forwardly by an amount equal to the thickness of each article that is removed. However, means are provided for increasing the positioning element's movement in response to removal of the last article, whereby a sensing means can more readily detect such movement to thereby cause an indication of an empty container.

8 Claims, 8 Drawing Figures

CONTAINER FOR DISPENSING ARTICLES TO AN AUTOMATED ANALYZER

BACKGROUND OF THE INVENTION

Cross-Reference to Related Applications

Reference is made to commonly assigned, copending U.S. Patent Application Ser. No. 751,912 entitled CHEMICAL ANALYZER, filed in the names of Louis C. Nosco, Anthony P. DiFulvio and Henry S. Adamski on Dec. 17, 1976, now abandoned; and Ser. No. 912,290 entitled ARTICLE DISPENSER APPARATUS, filed in the names of G. W. Scherer and R. G. Covington concurrently herewith.

Field of the Invention

The present invention relates to article containers from which individual articles can be sequentially removed from stacks of articles received in the containers.

Description of the Prior Art

In recent years, a number of automated systems have been developed for carrying out quantitative chemical analysis of fluid samples. While many of the commercially available systems utilize liquid reagents and require analyzer equipment having intricate solution handling and transport capabilities, one biological fluid analyzing apparatus in which discrete test slides containing individual dry reagents are metered through the apparatus to receive a drop of biological fluid to be tested is described in commonly assigned, co-pending U.S. Patent Application Ser. No. 751,912, entitled CHEMICAL ANALYZER filed on Dec. 17, 1976.

As described in that application, the test slides are stacked in containers, also called cartridges. Each slide in a particular container has the same, appropriate reagent for a particular test, such as for example a reagent for testing glucose in blood serum. Other containers might house slides for other tests. One or more container may be received in an appropriate nest of the analyzing apparatus with a spring biased plunger arranged to enter the container through an opening. The plunger engages a movable element located in the container behind the slide stack to urge the slides forwardly toward a dispensing station at one end of the container. An example of such containers is disclosed in commonly assigned, copending U.S. Patent Application Ser. No. 912,290 entitled ARTICLE DISPENSER APPARATUS, filed in the names of G. W. Scherer and R. G. Covington concurrently herewith.

A push blade in the analyzing apparatus enters the container at the dispensing station to remove the leading slide from the container by pushing it through a slot in the container wall. The remaining slides are sequentially moved forwardly in the container by the plunger as each preceding slide is removed.

It is important that the chemical analyzer apparatus not be operated without slides. First, many of the quantitative chemical analysis tests performed by such apparatus relate to biological fluid and are often critical to a patient's health. Operation without a reagent slide would mandate that the test be re-run and thereby impose unnecessary delay in the diagnosis process. A second reason for insuring that a slide be present in the apparatus is that the slides are intended to receive a drop of the fluid to be tested. If no slide is present, that fluid can end up elsewhere in the apparatus to perhaps promote a contamination problem. The present invention relates to a container which has an easily detectable characteristic when the last article is dispensed therefrom.

SUMMARY OF THE INVENTION

In accordance with the present invention, a container for receiving a stack of reagent articles for sequential forward movement toward, and removal from, a dispensing end of the container for delivery to apparatus for carrying out quantitative chemical analysis of fluid samples includes means for providing an easily detectable configuration change when the last article is removed. A stack positioning element engages one end of the article stack and moves a predetermined distance each time any but the last article is removed and moves a distance different than the predetermined distance when the last article is removed.

In a preferred embodiment of the present invention, the received articles are urged into abutment against a surface of the container to position the foremost slide at the container's dispensing station. A stack positioning element behind the received article stack urges the article stack toward the dispensing station and moves forwardly in the container by a distance equal to the thickness of each article being removed. An abutment surface on the stack positioning element contacts the rearmost article and is positioned out of alignment with the abutment surface of the container. Accordingly, when the last of the articles has been removed from the container, the abutment surface of the stack positioning element moves past the abutment surface of the container, permitting the element to move forwardly in the container by an amount greater than the thickness of the last removed article. This increased movement of the stack is easily detectable by suitable means in the analyzer apparatus to signal the operator that the container is empty, to shut off the analyzer and/or to perform some other suitable operation.

The invention, and its objects and advantages, will become more apparent in the detailed description of the preferred embodiment presented below.

BRIEF DESCRIPTION OF THE DRAWINGS

In the detailed description of the preferred embodiment of the invention presented below, reference is made to the accompanying drawings in which.

DESCRIPTION OF THE PREFERRED EMBODIMENTS

Figure 1:
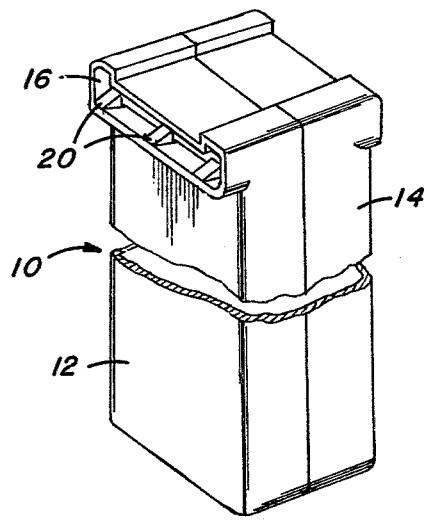
FIg. 1 is a perspective view of a slide container apparatus in accordance with a preferred embodiment of the present invention.
Figure 2:
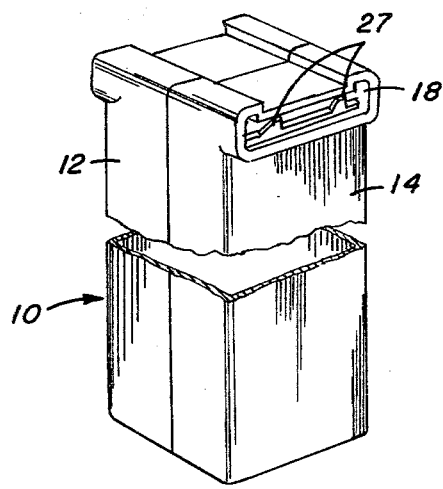
FIG. 2 is a perspective view of the apparatus of FIG. 1 taken from another angle.

In accordance with an illustrative embodiment of the present invention there is shown in FIGS. 1 and 2 a container, designated by the reference numeral 10, adapted to hold a stack of test slides for supply to a chemical analyzer such as the analyzer disclosed in aforementioned U.S. Patent Application Ser. No. 751,912. Container 10 includes a generally rectangular casing having two parts 12 and 14 shown separated in FIG. 3 and is shaped to be received in a nest (not shown) of the analyzer.

Figure 3:
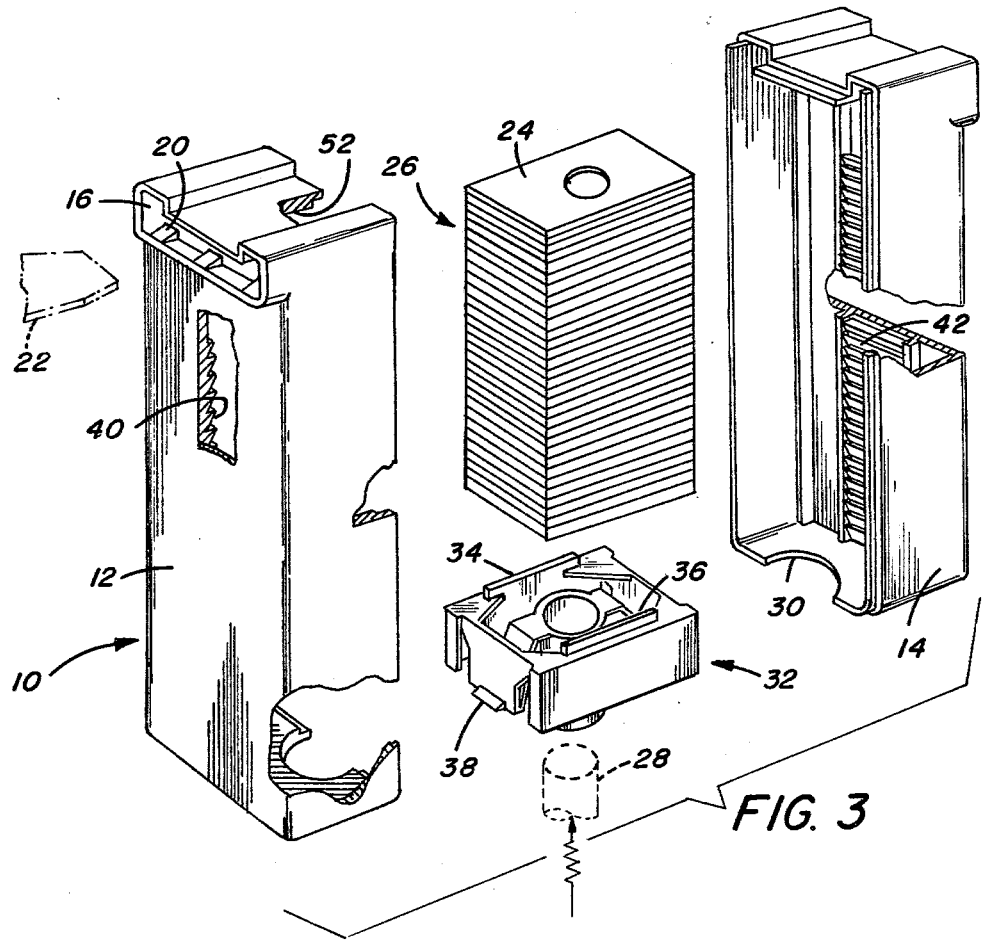
FIG. 3 is an exploded view of the apparatus of FIG. 1 showing a slide stack and a stack positioning element.

A dispensing station is provided at the forward end of container 10 (the top of the container as shown in FIGS. 1-3) and includes a pair of slots 16 and 18 for removing slides from the container. Slot 16 is ramped (three ramps 20 shown) to guide a push blade 22 (FIG. 3) of the analyzer into contact with the trailing edge of the forward-most slide 24 of a stack 26 of slides. Slot 18 has a pair of tabs 27 which normally retain the slides in the container until pushed out by blade 22. The push blade is adapted to extend through slot 16 to push the foremost slide out of slot 18 and into slide handling means, now shown, of the analyzing apparatus.

When push blade 22 is withdrawn from slot 16, slide stack 26 is indexed forwardly (upwardly in the drawings) by a spring-loaded plunger 28 which is received through an opening 30 in the rear (or bottom) wall of the container to push against a stack positioning element 32. The stack positioning element is described in detail in aforementioned application Ser. No. 912,290 filed concurrently herewith. Generally, the slide stack rests on a pair of rails 34 and 36 of the stack positioning element, which moves forwardly toward the dispensing station of container 10 as slides are removed from the container. A pair of anti-backup ratchet pawls 38 on either side of the stack positioning element engage successive teeth of ratchet teeth sets 40 and 42 respectively to inhibit movement of the slides rearwardly away from the dispensing station whenever the container is not in the analyzer nest. For example, should the container be taken from the analyzer nest after some but not all of the slides have been removed therefrom, plunger 28 would withdraw from opening 30 so that only the ratchet means keeps the slide stack from moving away from the dispensing station.

Figure 4:
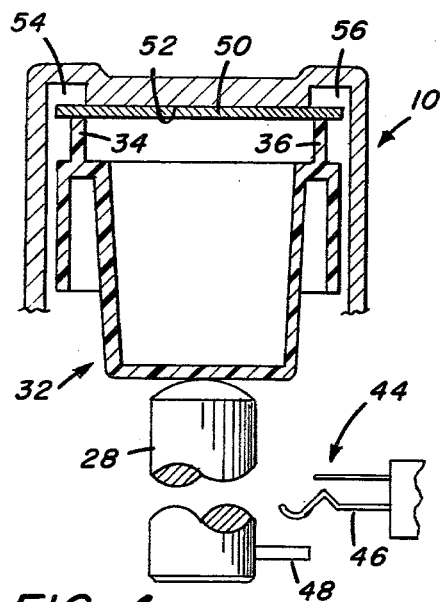
FIG. 4 is a cross-sectional view of the forward end of the apparatus of FIG. 1 with one slide in the container.
Figure 5:
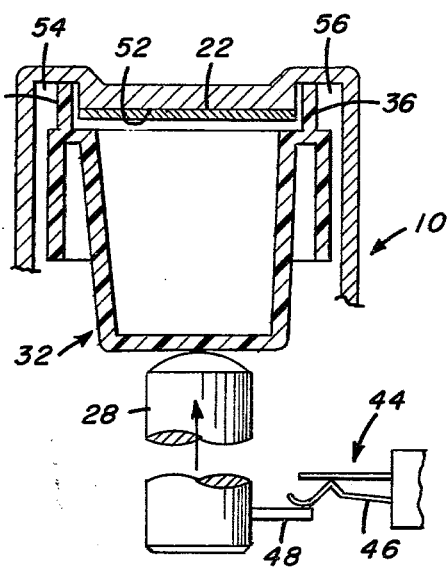
FIG. 5 is a cross sectional view similar to FIG. 4 without a slide in the container.

As mentioned hereinbefore, several advantages are derived by providing a mechanism for automatically detecting the absence of a slide in container 10. In FIGS. 4 and 5, we have schematically shown a portion of such a mechanism which could be provided in the analyzer apparatus to either alert the operator to the fact that container 10 is empty or to disable the analyzer until a fresh supply of slides has been provided. An electrical switch 44 has one contact 46 which lies in the path of a pin 48 extending from plunger 28. When the last slide 50 as shown in FIG. 4 has been removed from container 10, stack positioning element 32 is free to move forwardly in the container to the position shown in FIG. 5 to cause pin 48 to close switch 44. The switch may be electrically connected to any suitable apparatus for alerting the operator to the fact that the container is empty and/or for disabling the analyzer. Of course it will be obvious to those skilled in the art that other sensing and indication means, such as for example photoelectric means can be employed to provide such sensing and indication.

Referring once more to FIG. 4, it can be seen that the forward-most surface of slide 50 rests against an abutment surface 52 of the container. The rearmost surface of slide 50 is engaged by the ends of rails 34 and 36 which form second abutment surfaces spaced from first abutment surface 52 by the combined thicknesses of the slides therebetween.

As individual slides are removed from the container, the first and second abutment surfaces become progressively closer to each other until only one slide 50 remains in the container, as shown in FIG. 4. If the first and second abutment surfaces were aligned with each other along the direction of travel of the stack positioning element, removal of slide 50 from the container would cause the positioning element to move forwardly by an amount only equal to the thickness of slide 50, whereupon the ends of rails 34 and 36 would contact abutment surface 52. In one contemplated use of the apparatus in accordance with the present invention, the slides that make up stack 26 are approximately 1.1 millimeters thick. Therefore, if the first and second abutment surfaces were aligned, the final movement of the stack positioning element would be limited to about 1.1 millimeters, and that would be the amount of movement to be sensed by switch 44.

To provide a longer final movement a pair of recesses 54 and 56 are provided in the forward end of container 10 in alignment with rails 34 and 36. In order to maintain sufficient wall thickness of container 10, the wall may be relieved in the region of the recesses. When the last slide is withdrawn from container 10, stack positioning element 32 is free to move forwardly beyond the position where the ends of ribs 34 and 36 are in the plane of surface 52 of the container and into a position whereat the ribs extend into recessess 54 and 56 as shown in FIG. 5.

Recesses 54 and 56 may, for example, extend approximately 1.4 millimeters beyond abutment surface 52. Accordingly, upon removal of slide 50 from the container, positioning element 32 will move forwardly in the container from its FIG. 4 position to its FIG. 5 position, a total of approximately 2.5 millimeters if the slide and recess dimensions are as described above. It is apparent that a movement of pin 48 of 2.5 millimeters is much easier to detect than a 1.1 millimeter movement corresponding to the thickness of slide 50. By provision of the additional movement of pin 48, a less sensitive switch 44 may be used and the position of the switch in the analyzer apparatus is less critical. Therefore, manufacture is simplified and reliability increased.

In the embodiment shown in FIGS. 1-5, and as particularly seen in FIG. 5, provision has been made to allow push blade 22 to pass through container 10 without engaging stack positioning element 32 or any other obstruction when the supply of slides has been exhausted. This provision is particularly important when the container is used in analyzer apparatus wherein engagement of push blade 22 with a fixed obstruction would result in damage to the push blade mechanism.

However, it is foreseeable that some analyzer apparatus might not be of the type in which damage would occur by engagement of the push blade with an obstruction. For example, some analyzer apparatus might include a clutch mechanism between the push blade and its drive means.

Figure 6:
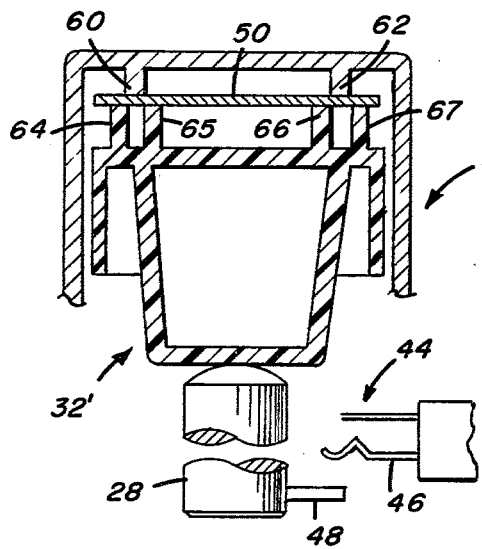
FIGS. 6, 7 and 8 are views similar to FIGS. 4 and 5 showing a second embodiment of the present invention.
Figure 7:
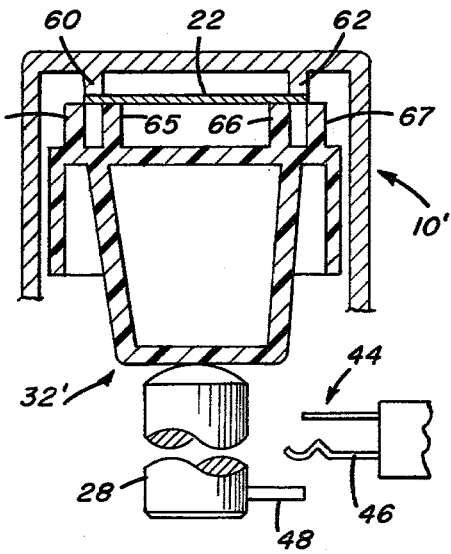
Figure 8:
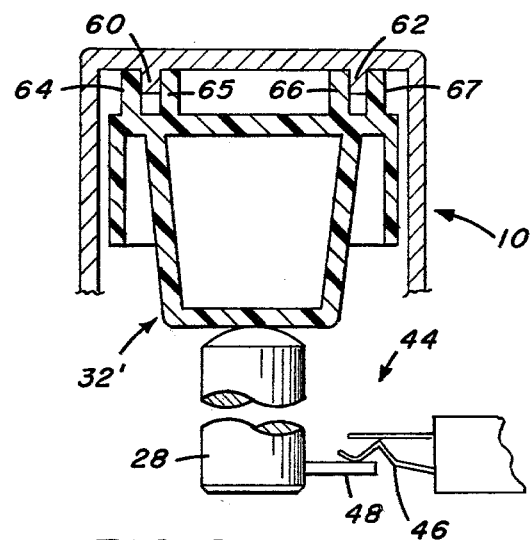

In FIGS. 6-8, we have shown slide container apparatus wherein provision has not been made for the push blade to clear the stack positioning element when there are no slides in the container. Those parts of the container and stack positioning element which are similar to those of the embodiment shown in FIGS. 1-5, have been referred to by the same reference numerals as used in the first embodiment. However, a prime mark has been added to those numerals in FIGS. 6-8 which refer to features similar but not identical to the corresponding feature in FIGS. 1–5.

In FIG. 6, we have shown a single slide 50 in container 10' forward of a stack positioning element 32'. A pair of ribs 60 and 62 project rearwardly from the front container wall to define first abutment surfaces against which slide 50 is located by second abutment surfaces defined by four ribs 64–67 on stack positioning element 32'. When blade 22 enters the container as shown in FIG. 7 to push slide 50 out of the container, the stack positioning element moves slightly forward in the container because push blade 22 is somewhat thinner than slide 50. Now, when blade 22 is withdrawn from the container, the stack positioning element moves further in the container to the position shown in FIG. 8, to cause pin 48 to close switch 44 and thereby signal the existance of an empty container.

Should the dispensing mechanism be reactivated so that push blade 22 reenters an empty container as depicted in FIG. 8, the blade will engage ribs 65 and 66 and be blocked thereby. It is assumed that the mechanism activating the push blade is provided with some device to prevent damage to the mechanism upon occurrence of such engagement. Such a device might take the form of a friction clutch or similar apparatus which would disengage the push blade from its drive mechanism.

The invention has been described in detail with particular reference to preferred embodiments thereof, but it will be understood that variations and modifications can be effected within the spirit and scope of the invention.

What is claimed is:

1. A container for receiving and dispensing reagent articles of predetermined thickness to apparatus having a movable actuator and adapted to use the articles to carry out quantitative chemical analysis of fluid samples, said container comprising:
   a casing having a chamber adapted to receive a stack of the articles and having an article dispensing station at which articles may be removed from said chamber for delivery to the apparatus;
   a movable stack positioning element in said chamber engageable with one end of a received article stack to urge the stack toward said dispensing station whereby the articles may be removed individually from the dispensing station and succeeding articles moved sequentially into alignment with the dispensing station, said stack positioning element being movable by the actuator a predetermined distance each time any but the last article is removed from said dispensing station; and
   means for causing said element to be moved a distance different from said predetermined distance when the last article is removed from said dispensing station.

2. A container as set forth in claim 1 wherein said distance different from said predetermined distance is substantially greater than said predetermined distance.

3. A container as set forth in claim 1 wherein said predetermined distance is equal to the thickness of the received articles.

4. A container articles of predetermined thickness to apparatus adapted to use the articles to carry out quantitative chemical analysis of fluid samples, said container comprising:
   a casing having a dispensing station and a chamber adapted to receive a stack of the articles for movement in a forward direction toward, and sequential removal from, said dispensing station for delivery to the apparatus;
   a first abutment surface on said container and adapted to be engaged by the forward-most article to align that article with said dispensing station;
   a stack positioning element movable forwardly in said chamber and engageable with one end of the stack to urge the forward-most article against said first abutment surface, whereby the forward-most article may be removed from the dispensing station and succeeding articles may be moved sequentially into alignment with the dispensing station under the influence of said stack positioning element; and
   a second abutment surface on said stack positioning element for engaging the rear-most article of the stack, said first and second abutment surfaces being positioned such that, upon the removal from said cartridge of the rear-most article, said stack positioning element is free to move a distance greater than the thickness of the rear-most article to a position whereat said second abutment surface is positioned forward of said first abutment surface.

5. A container as set forth in claim 4 wherein:
   said casing has at least one recess adjacent to said first abutment surface; and
   said stack positioning element has a projection the end of which defines said second abutment surface, said projection being aligned with said recess, whereby said projection is free to enter said recess when the rear-most article is removed from said dispensing station.

6. A container as set forth by claim 4 wherein said casing further has a slot through which the articles may be removed, said slot being aligned with said first abutment surface in a direction lateral to the direction of movement of the articles.

7. A container as set forth in claim 4 wherein:
   said casing has a first projection extending into said chamber, the end of said projection defining said first abutment surface; and
   said stack positioning element has a second projection extending toward said first projection, the end of said second projection defining said second abutment surface.

8. A container for receiving and dispensing reagent articles of predetermined thickness to apparatus including sensing means for detecting movement and adapted to use the articles to carry out quantitative chemical analysis of fluid samples, said container comprising:
   a casing having a dispensing station and a chamber adapted to receive a stack of the articles for movement in a forward direction toward, and sequential removal from, said dispensing station for delivery to the apparatus;
   a first abutment surface on said container positioned to be engaged by the forward-most article to align that article with said dispensing station;
   a stack positioning element movable toward said dispensing station in said chamber and engageable with one end of the stack to urge the forward-most article against said first abutment surface, whereby the forward-most article may be removed from the dispensing station and succeeding articles may be moved sequentially into alignment with the dispensing station under the influence of said stack positioning element; and a second abutment surface on said stack positioning element for engaging the rear-most article of the stack, said first and second abutment surfaces being positioned such that, upon the removal from said cartridge of the rear-most article, said stack positioning element is free to move a distance greater than the thickness of the rear-most article to a position whereat said second abutment surface is positioned forward of said first abutment surface, whereby the sensing means of the apparatus may detect the movement of said element.

* * * * *